United States Patent [19]

Paul et al.

[11] 4,184,936

[45] Jan. 22, 1980

[54] DEVICE FOR DETERMINING IONIC ACTIVITY

[75] Inventors: John O. Paul, East Rochester; Kerinchan Babaoglu, Penfield, both of N.Y.

[73] Assignee: Eastman Kodak Company, Rochester, N.Y.

[21] Appl. No.: 927,085

[22] Filed: Jul. 24, 1978

[51] Int. Cl.² .................. G01N 27/46; G01N 27/58
[52] U.S. Cl. ........................ 204/195 R; 204/195 M
[58] Field of Search ........ 204/195 R, 195 M, 195 B, 204/1 T

[56] References Cited
U.S. PATENT DOCUMENTS

| 2,962,426 | 11/1960 | Sharpsteen | 204/1 T |
|---|---|---|---|
| 3,261,668 | 7/1966 | Natelson | 23/253 |
| 3,855,100 | 12/1974 | Haddad | 204/195 F |
| 4,053,381 | 10/1977 | Hamblen et al. | 204/195 M |

*Primary Examiner*—G. L. Kaplan
*Attorney, Agent, or Firm*—Milton S. Sales

[57] ABSTRACT

A device is disclosed for determining ion activity in liquid solutions by the use of electrodes and a capillary bridge which promotes ionic migration between the electrodes. The bridge is formed of a porous material layer into which liquid solutions are absorbed, a bottom nonporous layer between the electrodes and the porous material, and a top nonporous layer on the other side of the porous material. Preferably, the three layers are apertured at each electrode to provide wells for receiving drops of liquid solutions, and the top layer is hydrophobic to retain the solution drops in the region of the apertures.

9 Claims, 2 Drawing Figures

DEVICE FOR DETERMINING IONIC ACTIVITY

BACKGROUND OF THE INVENTION

1. Field of the Invention

The present invention relates to devices useful in determining the activity of ions in a sample of liquid solution, and is particularly useful in potentiometrically measuring ion activity in drops of biological fluids.

2. Description of the Prior Art

There is a variety of apparatus in the prior art for measuring ion concentration in solutions. Typically such apparatus includes a reference electrode and an ion-selective electrode. When both the reference and the ion-selective electrodes are immersed into a solution to be analyzed, they constitute an electrochemical cell with an electrical potential developed across the electrodes. This electrical potential is proportional to the logarithm of the activity of the ions to which the ion-selective electrode is sensitive.

An ion-selective electrode test device which is both disposable and usable with drop-sized test samples is shown in commonly assigned U.S. Pat. No. 4,053,381 which issued to D. P. Hamblem et al on Oct. 11, 1977. Two solid electrodes are mounted on a frame, and a capillary bridge is provided for promoting ionic migration between the electrodes upon application of one or more liquid drops to each electrode. The capillary bridge includes a support layer and a porous layer with ionic access to both electrodes. When a drop of liquid is applied to each electrode, the drops spread into the capillary bridge until contact is made at a thin junction interface, permitting ionic migration between the drops. Preferably a reference solution of known ion activity is applied to one (reference) electrode and the test sample solution is applied to the other electrode. The electrical potentials at the interfaces between the drops of liquid and the electrodes are measured and compared to provide an indication of ion activity in the test sample solution.

Although the device disclosed in U.S. Pat. No. 4,053,381 provides excellent results in use for determining ion activity in liquids, some problems arise with respect to the degree of care which must be exercised during operation. For example, it is highly desirable that the capillary bridge absorb a fairly exact amount of liquid. Too much absorption leaves insufficient liquid at the electrodes, while too little absorption might result in spill over onto the electrodes. Controlled absorption provides a reproducible fluid junction location and forming time within the bridge.

Another adverse situation might arise by the liquid placed in the region of the electrodes spreading, not only within the capillary bridge, but also across the top surface of the bridge. This, on occasion, may result in the formation of an apparent junction on top of the bridge, causing liquid mixing and variable readings. Such a situation will be referred to herein as "external bridging" of the capillary bridge.

Another possible cause for imprecision is evaporation of liquid from the drops. Even though evaporation of the test and reference solutions would normally occur at the same rate, changes in electrical potential due to changes in concentration would not necessarily cancel because of the presence of different interferents in the test and the reference solutions. The effect of such interferents may be amplified by evaporation.

By the present invention, we have provided an improvement in test devices such as described in U.S. Pat. No. 4,053,381, wherein absorption of the solution drops by the capillary bridge is controlled, external bridging is eliminated and evaporation losses are reduced. Additionally, test devices manufactured in accordance with the present invention exhibit exceptionally large drop placement latitude, i.e., a drop of liquid may be placed upon the device anywhere over a large area and still wet the electrode area. This feature is important in permitting relaxed manufacturing tolerances in automatic processing apparatus wherein the drops are applied mechanically.

SUMMARY OF THE INVENTION

The present invention provides a device for determining ion activity of a liquid test solution by means of ion-selective electrodes. A pair of electrodes are mounted on a frame and connected by a capillary bridge. The bridge includes a porous member on a nonporous support, and provides ionic flow between the electrodes upon application of one or more liquid drops at each electrode. The porous member is provided with a top nonporous cover layer which is preferably hydrophobic.

In a preferred embodiment of the present invention, the bridge takes the form of a trilaminate made up of a top hydrophobic layer, a middle absorbent layer and a bottom barrier layer with an adhesive to attach the bridge to the electrodes. Electrical contact is achieved by means of a hole through the bridge at each electrode to provide wells for the reference and test solutions. When drops are applied to fill the wells, excess liquid forms large caps contained by the hydrophobic top layer. The liquid in these caps is soon absorbed into the absorbent layer to form an ionic junction within the bridge.

Because the top cover layer is nonporous, absorption of the test solution by the capillary bridge is controlled and evaporation losses are reduced. The hydrophobic nature of the cover layer inhibits the solution from spreading across the bridge surface to cause external bridging and increases drop placement latitude.

The invention, and its objects and advantages, will become more apparent in the detailed description of the preferred embodiment presented below.

BRIEF DESCRIPTION OF THE DRAWINGS

In the detailed description of the preferred embodiment of the invention presented below, reference is made to the accompanying drawings in which.

DESCRIPTION OF THE PREFERRED EMBODIMENT

Although the invention as hereinafter described is directed to a device for potentiometrically determining ion activity through the use of ion-selective electrodes, such device can be used for other electrical tests of a liquid solution. The device is particularly adapted for processing by automated handling devices.

Figure 1:
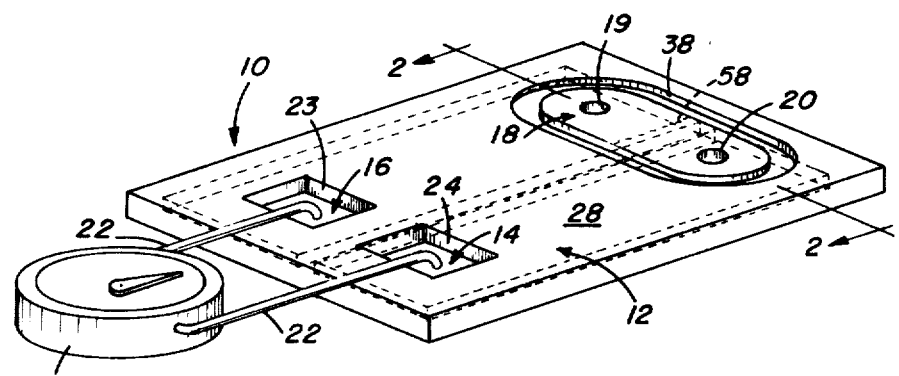
FIG. 1 is a perspective view of apparatus constructed in accordance with the invention.

Referring to FIG. 1, there is illustrated a device 10 which comprises a mounting frame 12, two solid electrode substrates 14 and 16 (shown partially in phantom)

which form part of a pair of electrodes mounted in the frame electrically isolated from each other, and a capillary bridge 18 for promoting ionic migration between liquid drops deposited on the electrodes in holes 19 and 20 which extend through the bridge. An electrometer 21 is connected by wires 22 to electrode substrates 14 and 16 through appropriate apertures 23 and 24 in frame 12 to permit comparison of potentials.

The Mounting Frame

Frame 12 comprises a generally planar body having bottom and top surfaces 26 and 28. As used herein, the words "bottom" and "top" refer to the preferred orientation of the device during normal use. The bottom of frame 12 is hollowed out at 36 (FIG. 2) to receive electrodes 30 and 32. The electrodes are positioned in the hollowed out region so as to be out of electrical contact with each other. Any convenient means may be used to hold the electrodes in the frame, such as by adhesive bonding. A transport passageway 38 is formed in frame 16 in direct communication with hollowed out region 36.

The Electrodes

For the potentiometric measurements disclosed herein, the electrodes preferably include an ion-selective electrode and an external reference electrode, for a direct mode of determining potentials, or two ion-selective electrodes for a differential measurement comparing the ion activity of an unknown test solution with that of a similar reference solution of known ion concentration. Electrodes 30 and 32 are shown as being identical and, therefore, suitable for the differential mode of measurement which is made by electrometer 21 when a test drop 42 is applied to one electrode and a reference drop 44 having a known concentration of ions is applied to the other electrode. In the drawings, the thickness of the layers of the electrodes has been greatly exaggerated for clarity.

Both electrodes are formed of layers comprising an ion-selective membrane 46 (permeable to the ion of choice) coated over an internal reference element and a support 47, all of which are solid layers preferably in a dried condition. The internal reference element is shown as comprising several layers such as metal layers 14 (electrode 30) and 16 (electrode 32), layer 48 which is an insoluble salt of the metal of layers 14 and 16, and layer 49 which is an electrolyte containing layer. Although the layers are generally referred to as being "coated" one over another, it should be understood that the term "coating" is meant to include laminating or otherwise forming the various strata one over another by any technique.

For purposes of describing the present invention, it is believed that a detailed discussion of the structure and operation of electrodes 30 and 32 is not necessary. However, a full description of various embodiments of such electrodes and the method of use thereof may be found in hereinbefore mentioned U.S. Pat. No. 4,053,381. The disclosure of that patent is specifically incorporated herein by reference.

The Capillary Bridge

Figure 2:
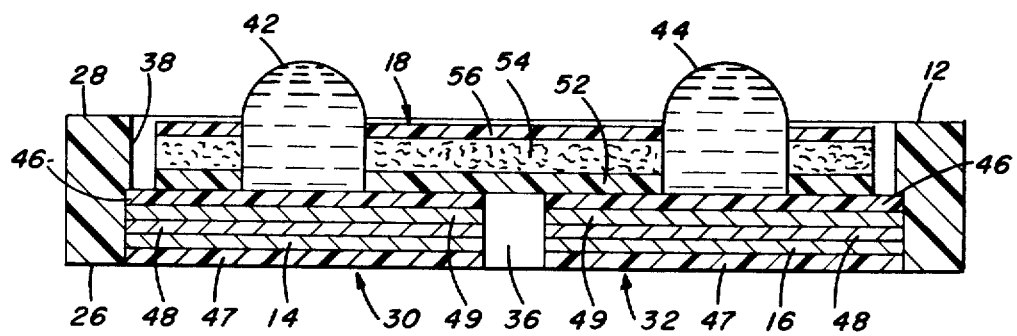
FIG. 2 is a sectional view taken generally along the line designated as 2—2 in FIG. 1, showing in detail a preferred form of the capillary bridge.

Capillary bridge 18, shown in section in FIG. 2, is a means of promoting ionic migration between electrodes 30 and 32. The capillary bridge can be formed of a three layer trilaminate of a variety of compositions. As shown, the bridge is preferably a flat, composite strip having holes 19 and 20, FIG. 1, where the drops of liquid solution 42, 44 are applied. The capillary bridge comprises a bottom support layer 52 which is nonporous, a middle porous or absorbing layer 54, and a top nonporous and hydrophobic layer 56.

Middle layer 54 in a preferred embodiment is a porous paper into which liquid drops 42 and 44 are absorbed to form an ionic junction 58. A suitable paper for correct absorption of human serum is Whatman #2 chroma, 0.007 inch thick, which is manufactured in the United Kingdom by W. and R. Balston, Ltd. When spotted with a liquid solution drop at holes 19 and 20, the liquid fills the punched holes or wells, forms large caps on top layer 56 and, within 10 to 30 seconds, is absorbed into the paper. The liquid from each drop spreads into the capillary bridge until contact is made at about the middle of the bridge to form an ionic junction. Sufficient liquid is left unabsorbed to fill the wells. Another example of a material suitable for the middle, porous layer is disclosed in referenced U.S. Pat. No. 4,053,381.

Bottom layer 52 and top layer 56 are nonporous barriers to liquid except at holes 19 and 20. The top and bottom layers are preferably high-density polyethylene coated on the middle layer, with an adhesive applied to the bottom layer for attachment to the electrodes. One suitable polyethylene is Tenite NP31 manufactured by the Eastman Kodak Company of Rochester, N.Y. Alternatively the top and bottom layers may be commercially available adhesive tape such as double-sided Scotch brand transparent tape No. 665 for the bottom layer and single-sided Highland brand transparent tape No. 5910 for the top layer, both manufactured by the 3M Company of St. Paul, Minn.

It is important that the liquid solution not contact the peripheral edges of electrodes 30 and 32, which would cause a short across the electrode layers. Accordingly, bottom layer 52 is desirably thick enough (approximately 4 mil in a preferred embodiment) to prevent fibers from middle layer 54 bridging across the bottom layer to electrodes 30 and 32. That thickness is not necessary for top layer 56, which may be approximately 1.5 mil thick to conserve space. However, if the top layer is a different thickness than the bottom layer, the capillary bridge may tend to curl. Should this present a problem, the curl can be prevented by forming top layer 56 of higher density material than bottom layer 52. Alternatively, the thickness of the top layer may be increased to more closely equal that of the bottom layer.

Operation

Operation of the device is described in hereinbefore identified U.S. Pat. No. 4,053,381, but in general proceeds by spotting a drop of the reference solution in hole 19 and a drop of the test solution in hole 20. Probes 22 contact layers 14 and 16 of electrodes 30 and 32, respectively, and the potentials are read on electrometer 21. The reading indicates ion activity in the test solution. The frame mount is then removed from contact with electrometer 21 and disposed of, and a new frame with its electrodes is positioned to receive subsequent drops of solution and to contact the electrometer leads.

Advantages of Hydrophobic Top Layer

As set forth hereinbefore, the nonporous and hydrophobic characteristics of top layer 56 provide controlled absorption of the test liquid, elimination of external bridging, reduction of evaporation, and improved drop placement latitude. Table I summarizes precision test results during experiments on devices made with a bottom layer 52 of double-sided Scotch adhesive tape No. 665 and a middle porous layer 54 of Whatman #2 chroma paper. Some of the devices were provided with a top layer 56 of Highland adhesive tape No. 5910, while other devices had no top layer. A 0.109 inch hole was punched at each electrode on one centimeter centers. Readings of an electrometer attached as in FIG. 1 were taken after three minutes to allow sufficient time for the electrochemical reaction to stabilize. A second reading was taken after five minutes.

TABLE I

| Run Sample | Top Layer | Position | Signal (Millivolts) | | | |
|---|---|---|---|---|---|---|
| | | | Three Minutes | | Five Minutes | |
| | | | Mean | Std. Dev. | Mean | Std. Dev. |
| 1 | yes | centered | 11.3 | ±0.6 | 11.5 | ±0.6 |
| 2 | no | centered | 12.4 | ±2.0 | 12.9 | ±2.4 |
| 3 | yes | displaced | 11.4 | ±0.4 | 11.4 | ±0.4 |
| 4 | no | displaced | 10.0 | ±1.2 | 9.4 | ±0.5 |

A comparison of the reading after three and five minutes gives an indication of the stability of the signal. It will be noted that the standard deviation in runs 1 and 3 did not change over the test period, while the standard deviation of runs 2 and 4 changed markedly. Likewise the mean values of runs 1 and 3 were more consistent than those for runs 2 and 3, and were closer to the theoretical value of 11.58 millivolts. Since runs 1 and 3 were made with capillary bridges with hydrophobic top layers and runs 2 and 3 were made with capillary bridges without such top layers, it appears from the results that the electrical signals generated are more reproducible when the bridge is provided with a hydrophobic top layer.

The column in Table I entitled "position" indicates whether the capillary bridges were mounted in a normal position on the electrodes so as to be spotted in the centers of holes 19 and 20 (runs 1 and 2) or displaced laterally approximately 0.02 inch (runs 3 and 4). A comparison of runs 1 and 3 indicates that there is no significant differences in response between the normally positioned bridge and the displaced bridge if provided with a hydrophobic top layer. However, without the top layer, significant differences in response were noted between the runs with normally placed bridges and the runs with displaced bridges (runs 2 and 4). These results indicate that there is greater positioning error latitude and drop placement latitude for capillary bridges with hydrophobic top layers than for capillary bridges without hydrophobic top layers. This is of concern because of the tolerances associated with the placement of the bridge on the electrodes during manufacture and the positioning of the test device in the analyzer apparatus. Runs 1 and 2 consist of 25 samples each and runs 3 and 4 of 8 samples.

The advantage of providing a hydrophobic top layer in attaining greater drop placement latitude is further illustrated by Table II. The latitude limit assumed in Table II is that distance at which a drop placed on the capillary bridge failed to wet a hole in the bridge. The drops were injected from various heights from 0.05 inch to 0.07 inch above the bridge using stainless steel needles.

TABLE II

| | Drop Placement Latitude |
|---|---|
| With Top Layer | ±0.02 inch |
| Without Top Layer | none |

Table II illustrates that capillary bridges with hydrophobic top layers exhibited satisfactory drop placement latitude up to 0.02 inch of misalignment, whereas bridges without the top layer exhibited negligible placement latitude. Accordingly, the topless bridge would impose more stringent demands on device assembly and analyzer drop placement tolerances.

In the successful operation of a capillary bridge, it is necessary that the bridge absorb a fairly exact amount of liquid. Too much absorption results in insufficient unabsorbed liquid to keep holes 19 and 20 filled after the bridge is saturated. Not enough absorption leaves an excess of liquid on top of the bridge which may spill over onto the electrodes, shorting over the electrode sides.

By providing a hydrophobic cover layer, controlled absorption is achieved in the capillary bridge because the drops are formed into large caps and gradually absorbed into porous layer 54. Without the hydrophobic layer, the drops would spread laterally across the top of the bridge in a random and unpredictable manner (possibly at the expense of hole filling).

External bridging, as defined hereinbefore, is also a potential problem in capillary bridges. Without top hydrophobic layer 56, drops 42 and 44 not only would be absorbed into porous layer 54 at holes 19 and 20, but would also spread across the top surface of the bridge. If a liquid junction forms between the liquid spreading across the top surface, liquid mixing may result. The hydrophobic nature of top layer 56 inhibits external junction formation because the liquid prefers to wet porous layer 54 rather than spread across the hydrophobic surface.

As set forth in the "Description of the Prior Art" section of this specification, evaporation of liquid from the bridge during testing should be avoided or at least minimized. As shown in Table III, the provision of top layer 56 reduces evaporation losses from the bridge by about 3% at 70° F. and 17% at 100° F. as compared to losses from a bridge without a top layer.

TABLE III

| | Percent Evaporation | | | |
|---|---|---|---|---|
| | 70° F. | | 100° F. | |
| Lapsed Time | With Top Layer | Without Top Layer | With Top Layer | Without Top Layer |
| 1 min. | 2.2 | 2.4 | — | — |
| 3 min. | 6.0 | 6.5 | 24 | 33 |
| 5 min. | 9.5 | 12.5 | 37 | 54 |

The invention has been described in detail with particular reference to a preferred embodiment thereof, but it will be understood that variations and modifications can be effected within the spirit and scope of the invention.

What is claimed is:

1. A device having a frame and two solid electrodes mounted on the frame for determining the activity of ions in a liquid solution, said device comprising:
   means, including a porous member extending between the electrodes, for providing ionic flow between the electrodes upon application of liquid solution at each electrode;

a nonporous layer partially covering said porous member and spaced from said electrodes whereby liquid solution can be applied to said porous member at the electrodes, said nonporous layer inhibiting the loss of liquid solution from said porous member; and anti-shorting means for inhibiting the solution from contacting the edges of the electrodes.

2. A device as defined in claim 1 wherein said layer has holes therethrough aligned with the respective electrodes to receive the liquid solution.

3. A device having a frame and two solid electrodes mounted on the frame for determining the activity of ions in a liquid solution, said device comprising:

means, including a porous member extending between the electrodes, for providing ionic flow between the electrodes upon application of liquid solution at each electrode;

a hydrophobic layer partially covering said porous member and spaced from said electrodes whereby liquid solution can be applied to said porous member at the electrodes, said layer (1) being a liquid barrier, (2) having holes therethrough aligned with the respective electrodes to receive liquid solution, and (3) by its hydrophobic characteristic inhibiting liquid from spreading on the layer; and anti-shorting means for inhibiting the solution from contacting the edges of the electrodes.

4. A device as defined in claim 3 wherein said porous member has holes aligned with said holes in said hydrophobic layer for providing wells for receiving liquid solution.

5. A device having a frame and two solid electrodes mounted on the frame for determining the activity of ions in a liquid solution, said device comprising:

a frame;

two solid electrodes mounted on said frame;

means, including a porous member extending between the electrodes, for providing ionic flow between the electrodes upon application of liquid solution at each electrode; and first and second nonporous layers on opposite sides of said porous member for inhibiting the loss of liquid solution from said porous member, said first nonporous layer being positioned between said porous member and the electrodes and having holes therethrough aligned with the respective electrodes for providing liquid access between said porous member and said electrodes and said second nonporous layer partially covering said porous member whereby liquid solution can be applied to said porous member at the electrodes.

6. A device as defined in claim 5 wherein said second layer is (1) hydrophobic for inhibiting spreading of the liquid solution over the surface of said second layer and (2) has a hole therethrough aligned with each hole in said first layer.

7. A device as defined in claim 5 wherein:

said second layer is (1) hydrophobic for inhibiting spreading of the liquid solution over the surface of said second layer and (2) has a hole therethrough aligned with each hole in said first layer; and said porous member has holes aligned with said holes in said first and second nonporous layers for providing wells for receiving liquid solution.

8. A device as defined in claim 5 wherein:

said porous member comprises a fibrous material; and said first layer has a thickness sufficient to prevent fibers of said porous member from bridging the edge of said first layer and contacting the electrodes.

9. A device as defined in claim 5 wherein:

said porous member comprises a fibrous material; and said first layer has a thickness sufficient to prevent fibers of said porous member from bridging the edge of said first layer and contacting the electrodes; and said second layer is (1) thinner than said first layer to conserve space and (2) formed of a denser material than said first layer to prevent curling.

* * * * *